United States Patent
Brouillette et al.

(10) Patent No.: US 12,279,783 B2
(45) Date of Patent: Apr. 22, 2025

(54) COMBINED NON-INVASIVE AND MINIMALLY INVASIVE MECHANICAL ENERGY TARGETING

(71) Applicant: Les Solutions Medicales Soundbite Inc., Saint-Laurent (CA)

(72) Inventors: Martin Brouillette, Sherbrooke (CA); Steven Dion, Sherbrooke (CA); Louis-Philippe Riel, Montréal (CA); Steven Arless, Baie d'Urfé (CA); Marwan Abboud, Pierrefonds (CA); Dustin Arless, Vaudreuil-Dorion (CA)

(73) Assignee: LES SOLUTIONS MÉDICALES SOUNDBITE INC., Saint-Laurent (CA)

( * ) Notice: Subject to any disclaimer, the term of this patent is extended or adjusted under 35 U.S.C. 154(b) by 128 days.

(21) Appl. No.: 16/769,920

(22) PCT Filed: Dec. 10, 2018

(86) PCT No.: PCT/IB2018/059831
§ 371 (c)(1),
(2) Date: Jun. 4, 2020

(87) PCT Pub. No.: WO2019/111239
PCT Pub. Date: Jun. 13, 2019

(65) Prior Publication Data
US 2020/0383692 A1      Dec. 10, 2020

Related U.S. Application Data

(60) Provisional application No. 62/596,200, filed on Dec. 8, 2017.

(51) Int. Cl.
*A61B 17/22* (2006.01)
*A61B 17/00* (2006.01)
*A61B 17/225* (2006.01)

(52) U.S. Cl.
CPC ........ *A61B 17/2202* (2013.01); *A61B 17/225* (2013.01); *A61B 2017/00411* (2013.01);
(Continued)

(58) Field of Classification Search
CPC .............. A61B 17/2202; A61B 17/225; A61B 2017/00411; A61B 2017/00557;
(Continued)

(56) References Cited

U.S. PATENT DOCUMENTS 5,595,178 A      1/1997  Voss et al.
5,676,692 A  *  10/1997  Sanghvi ................. A61N 7/022
                                                                   601/3
(Continued)

FOREIGN PATENT DOCUMENTS

CN          101686830 A        3/2010
DE            3930600 A  *    4/1991   ............. A61B 17/22
(Continued)

OTHER PUBLICATIONS

Bakhru, R., et al., "I. Physics, Equipment, and Image Quality," ATS Seminars. vol. 10(5), 2013. p. 540-548 (Year: 2013).*
(Continued)

*Primary Examiner* — Sean A Frith
(74) *Attorney, Agent, or Firm* — Scully, Scott, murphy & Presser, P.C.

(57) ABSTRACT

A system for delivering mechanical waves to treat a lesion present in a vessel of a body, including an external mechanical wave source for generating mechanical waves from outside of the body, and a wave directing device insertable in the vessel, the wave directing device configured to receive the mechanical waves generated by the external mechanical wave source and to redirect the mechanical waves according to a target direction.

17 Claims, 5 Drawing Sheets

(52) U.S. Cl.
CPC ........... *A61B 2017/00557* (2013.01); *A61B 2017/22014* (2013.01); *A61B 2017/22024* (2013.01); *A61B 2017/22051* (2013.01)

(58) Field of Classification Search
CPC ......... A61B 2017/22014; A61B 2017/22024; A61B 2017/22051
See application file for complete search history.

(56) References Cited

U.S. PATENT DOCUMENTS

| | | | |
|---|---|---|---|
| 2005/0070961 A1* | 3/2005 | Maki | A61N 7/02 607/2 |
| 2006/0116671 A1* | 6/2006 | Slayton | A61N 7/02 606/27 |
| 2007/0004984 A1* | 1/2007 | Crum | A61B 8/12 600/471 |
| 2007/0276217 A1 | 11/2007 | Brown et al. | |
| 2009/0275866 A1* | 11/2009 | Gelbart | A61B 17/2256 601/4 |
| 2011/0034832 A1* | 2/2011 | Cioanta | G10K 11/28 601/1 |
| 2011/0282249 A1* | 11/2011 | Tsoref | A61N 7/00 601/2 |
| 2013/0197555 A1* | 8/2013 | Schaer | A61N 7/022 606/170 |
| 2014/0046339 A1 | 2/2014 | Bonutti | |
| 2014/0221828 A1* | 8/2014 | McKinnis | A61B 8/481 600/431 |
| 2014/0350401 A1* | 11/2014 | Sinelnikov | A61N 7/022 606/169 |
| 2015/0045724 A1* | 2/2015 | Chen | A61K 41/0047 604/22 |
| 2017/0136266 A1* | 5/2017 | Carol | A61N 7/022 |
| 2017/0209708 A1* | 7/2017 | Schwarz | A61N 2/004 |

FOREIGN PATENT DOCUMENTS

| | | |
|---|---|---|
| DE | 3930600 A1 | 4/1991 |
| EP | 2528653 A1 | 12/2012 |
| WO | 2013119662 A1 | 8/2013 |

OTHER PUBLICATIONS

Opielinski, K., et al., "Ultrasound transmission tomography image distortions caused by the refraction effect," Ultrasonics. vol. 38, 2000. p. 424-429 (Year: 2000).*
International Search Report; Canadian Intellectual Property Office; International Application No. PCT/IB2018/059831; Mar. 6, 2019; 4 pages.
Written Opinion of the International Searching Authority; Canadian Intellectual Property Office; International Application No. PCT/IB2018/059831; Mar. 6, 2019; 6 pages.

* cited by examiner

COMBINED NON-INVASIVE AND MINIMALLY INVASIVE MECHANICAL ENERGY TARGETING

CROSS REFERENCE TO RELATED APPLICATIONS

This application is a U.S. National Phase of International PCT Application No. PCT/IB2018/059831 filed Dec. 10, 2018, which claims the benefit of U.S. Provisional Patent Application Ser. No. 62/596,200 filed Dec. 8, 2017, the contents of each application are incorporated herein by reference in their entirety.

TECHNICAL FIELD

The present invention relates to the field of medical devices, specifically medical devices and systems using mechanical waves, such as ultrasound and shock waves, to perform medical treatment on cells, tissues and/or organs.

BACKGROUND

Non-invasive therapies using ultrasound or shock waves are commonly used to treat a variety of medical conditions, such as kidney stones and prostate cancer, for example. They are attractive because the source of mechanical waves is outside the body of the patient to be treated, so that the procedure may be considered as being non-invasive. By adequately designing the mechanical energy source, it is usually possible to focus the mechanical waves on a target to be treated within the body. However, there are some limitations to this technique. For example, the exact location of the target to be treated may be difficult to obtain due to limitations of the imaging method used. Also, the energy may not be focused at the exact desired target location due to physical limitations of the focusing wave itself and heterogeneities within the various tissues and organs into which the wave is propagating. In a further example, the energy density at the target may not be sufficient to accomplish the desired treatment.

Therefore there is a need for an improved method and device for delivering mechanical waves.

SUMMARY

According to a first broad aspect, there is provided a system for delivering mechanical waves to treat a lesion present in a vessel of a body, comprising: an external mechanical wave source for generating mechanical waves from outside of the body; and a wave directing device insertable in the vessel, the wave directing device for receiving the mechanical waves generated by the external mechanical wave source and redirecting the mechanical waves according to a target direction.

In one embodiment, the wave directing device is adapted to reflect and concentrate the mechanical waves received from the external mechanical wave source.

In one embodiment, the wave directing device comprises a least one section having one of a concave, hemi-spherical and parabolic shape.

In one embodiment, the wave directing device is one of made of and coated with a reflective material having an acoustic impedance being greater that an acoustic impedance of water.

In one embodiment, the wave directing device comprises an acoustic mirror.

In another embodiment, the wave directing device is adapted to refract the mechanical waves received from the external mechanical wave source.

In one embodiment, the wave directing device is made of a material having an acoustic impedance being different from an acoustic impedance of water.

In one embodiment, the wave directing device comprises an acoustic lens.

In one embodiment, the wave directing device comprises at least one marker visible on a medical image.

In one embodiment, the marker is made of a radiopaque material.

In one embodiment, the radiopaque material comprises one of platinum, gold, tungsten, a combination thereof and a polymer doped with one of said platinum, said gold and said tungsten.

In one embodiment, the wave directing device comprises an inflatable balloon, the system further comprising a source of fluid fluidly connected to the inflatable balloon for injecting a fluid within the inflatable balloon so as to change a shape of the balloon.

In one embodiment, the inflatable balloon is adapted to operate as an acoustic lens.

In one embodiment, the inflatable balloon is adapted to operate as an acoustic mirror.

In one embodiment, the system further comprises an elongated member, the wave directing device being secured to the elongated member.

In one embodiment, the wave directing device is removably secured to the elongated member.

In another embodiment, the wave directing device is integral with the elongated member In one embodiment, the elongated member comprises one of a balloon and a catheter.

In one embodiment, the system further comprises a position tracking device for tracking at least one of a position and an orientation of the wave directing device once inserted into the vessel of the body.

In one embodiment, the position tracking device comprises one of an X-Ray imaging device and an ultrasound imaging device.

In another embodiment, the position tracking device comprises a mechanical wave detector for detecting mechanical waves reflected by the wave directing device, the at least one of the position and the orientation of the wave directing device being determined according to at least one of an amplitude, a phase and a delay of mechanical waves detected by the mechanical wave detector.

In one embodiment, the wave directing device comprises a mechanically resonant structure for storing mechanical energy.

In one embodiment, the mechanically resonant structure comprises an inertia device and a compliant device.

In one embodiment, the wave directing device comprises at least one tube for one of aspirating debris and delivering a liquid.

In one embodiment, the wave directing device comprises a piezoelectric element for generating electricity.

According to another broad aspect, there is provided a method for treating a lesion, comprising: inserting a wave directing device into a vessel of a body, the vessel comprising a lesion to be treated; positioning the wave directing device adjacent to the lesion to be treated; generating mechanical waves using an external mechanical wave source located outside of the body and propagating the mechanical waves towards the wave directing device; and at the wave directing device, redirecting and concentrating the mechanical waves on the lesion to be treated.

In one embodiment, the step of redirecting the mechanical waves comprises reflecting the mechanical waves, the wave directing device being adapted to reflect and concentrate the mechanical waves received from the external mechanical wave source.

In one embodiment, the wave directing device comprises a least one section having one of a concave, hemi-spherical and parabolic shape.

In one embodiment, the wave directing device is one of made of and coated with a reflective material having an acoustic impedance being greater that an acoustic impedance of water.

In one embodiment, the wave directing device comprises an acoustic mirror.

In another embodiment, the step of said redirecting the mechanical waves comprises refracting the mechanical waves, the wave directing device being adapted to refract and concentrate the mechanical waves received from the external mechanical wave source.

In one embodiment, the wave directing device is made of a material having an acoustic impedance being different from an acoustic impedance of water.

In one embodiment, the wave directing device comprises an acoustic lens.

In one embodiment, the wave directing device comprises at least one marker visible on a medical image.

In one embodiment, the marker is made of a radiopaque material.

In one embodiment, the radiopaque material comprises one of platinum, gold, tungsten, a combination thereof and a polymer doped with one of said platinum, said gold and said tungsten.

In one embodiment, the wave directing device comprises an inflatable balloon, the method further comprising one of inflating and deflating the balloon to obtain a desired shape for the balloon prior to said generating the mechanical waves.

In one embodiment, the inflatable balloon is adapted to operate as an acoustic lens.

In another embodiment, the inflatable balloon is adapted to operate as an acoustic mirror.

In one embodiment, the wave directing device is secured to an elongated member and the step of positioning the wave directing device comprises manipulating a proximal end of the elongated member.

In one embodiment, the wave directing device is removably secured to the elongated member.

In another embodiment, the wave directing device is integral with the elongated member In one embodiment, the elongated member comprises one of a balloon and a catheter.

In one embodiment, the method further comprises detecting at least one of a position and an orientation of the wave directing device once inserted into the vessel using a position tracking device.

In one embodiment, the position tracking device comprises one of an X-Ray imaging device and an ultrasound imaging device.

In one embodiment, the step of detecting the at least one of the position and the orientation of the wave directing device comprises detecting mechanical waves reflected by the wave directing device using a mechanical wave detector and determining the at least one of the position and the orientation from at least one of an amplitude, a phase and a delay of mechanical waves detected by the mechanical wave detector.

In one embodiment, the wave directing device comprises a mechanically resonant structure for storing mechanical energy.

In one embodiment, the mechanically resonant structure comprises an inertia device and a compliant device.

In one embodiment, the wave directing device comprises at least one tube for one of aspirating debris and delivering a liquid.

In one embodiment, the wave directing device comprises a piezoelectric element for generating electricity.

For the purpose of the present description, a mechanical wave should be understood as a signal having arbitrary amplitude, duration, waveform, frequency, and/or the like. For example, a mechanical wave may have a high/low amplitude, a short/long duration, different waveforms, and any frequency content.

For the purpose of the present description, a mechanical pulse should be understood as a short duration mechanical wave. The duration of a mechanical pulse is of the order of $1/fc$.

In one embodiment, the mechanical pulse has a center frequency fc comprised between about 20 kHz and about 10 MHz. In one embodiment, the amplitude of the mechanical pulse when reaching the distal end of the catheter device is comprised between about 10 MPa and about 1000 MPa. In one embodiment, the duration of the mechanical pulse when reaching the distal end of the catheter device is in the order of $1/fc$.

In one embodiment, the amplitude of a mechanical pulse when reaching the distal end of the catheter device is comprised between about 1 MPa and about 1000 MPa. In one embodiment, the amplitude of the mechanical pulse when reaching the distal end of the catheter device is comprised between about 10 MPa and about 1000 MPa.

A shock wave is defined as a mechanical pulse having a short duration. i.e., a duration of the order of microseconds or less, and a high amplitude, i.e., an amplitude when reaching the distal end of the catheter device of at least 1 MPa.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
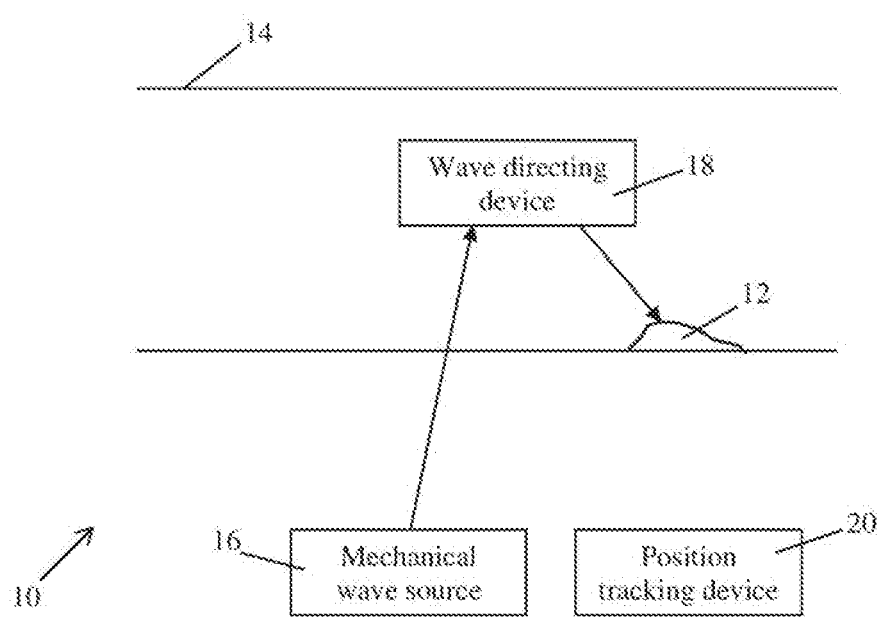
FIG. 1 is a block diagram illustrating a system comprising a source of mechanical waves for externally generating mechanical waves and a wave redirecting device for redirecting the generated mechanical waves towards a lesion to be treated present in a vessel of a body, in accordance with an embodiment.

FIG. 1 illustrates one embodiment of a system 10 for delivering mechanical waves or shock waves to treat a lesion 12 present in a blood vessel 14 such as an artery. The system 10 comprises a source 16 of mechanical waves or shock waves and a minimally-invasive wave directing device 18.

The wave generator 16 is positioned outside of the patient's body and is adapted to generate mechanical waves. The generated mechanical waves propagate through the patient's body up to the wave directing device 18. The wave directing device 18 is adapted to be inserted into the blood vessel 14 and positioned adjacent the lesion 12 to be treated. The wave directing device 18 is further adapted to redirect the mechanical waves received from the wave generator 16 towards the lesion 12. The redirected mechanical waves then propagate within the medium surrounding the wave directing device 18 toward the lesion 12. The mechanical waves further propagate into the lesion 12, which may create cracks within the lesion 12 or ablate the lesion 12, and eventually cleaves or breaks the lesion 12 into pieces or reduce its rigidity.

In one embodiment, the wave generator 16 is adapted to generate high amplitude and short duration pulses which propagate through the patient's body up to the wave directing device 18. The wave generator 16 may comprise at least one broadband source and/or at least one narrow band source. The narrow or broad band source may be an electromechanical transducer. The wave generator 16 may comprise a spatial concentrator to focus the output of at least one source toward the wave directing device 18.

It should be understood that the wave directing device 18 is shaped and sized so as to be inserted into the blood vessel 14 and to be moved within and along the blood vessel 14 up to the lesion 12. The wave directing device 18 may further be adapted to be oriented according to a desired orientation. For example, the wave directing device 18 may be adapted to be rotated. It should also be understood that any adequate device or apparatus and any adequate method for moving the wave directing device 18 within the blood vessel 14 may be used.

In one embodiment, the system 10 further comprises an elongated member, such as a flexible rod or tube, which is adapted to engage the wave directing device 18 and push the wave directing device 18 within the blood vessel 14 up to a position adjacent to the lesion 12. In one embodiment, the wave directing device 18 may be fixedly secured to the elongated member such as at the distal end of the elongated member. In another embodiment, the wave directing device 18 may be removably securable to the elongated member such as at the distal end of the elongated member. It should be understood that, when the wave directing device 18 is inserted into a vessel of a body, the proximal portion of the elongated member remains outside of the body and the proximal portion may be manipulated to position and orient the wave directing device 18 according to a desired position and orientation relative of the lesion 12 to be treated.

For example, the wave directing device 18 may be securable at the distal end of a catheter or a balloon. After being secured to the catheter or the balloon, the wave directing device is introduced into the blood vessel 14 and the catheter or balloon is pushed into the blood vessel 14 to position the wave directing device 18 adjacent to the lesion 12. In one embodiment, the catheter or balloon may also be rotated so as to adequately orient the wave directing device 18 relative to the lesion 12.

In another embodiment, the wave directing device 18 may be integral with a flexible rod or tube such as a catheter or a balloon. In this case, the wave directing device 18 may correspond to a portion of the flexible rod or tube which is adapted to redirect incoming mechanical waves.

In one embodiment, the system 10 further comprises a position tracking device 20 for tracking the position of the wave directing device 18 within the blood vessel 14 in order to adequately position and/or orient the wave directing device 18 relative to the lesion 12 to be treated. For example, the position tracking device 20 may be an imaging device for visualizing the wave directing device 18 while inserted in the patient's body. For example, the imaging device may be an X-ray imaging device. In this case, the wave directing device may be provided with a marker that is opaque to X-rays so as to be visible on X-ray images. The imaging device may also be an ultrasound imaging device, in which case the marker is highly reflecting of ultrasound energy. For example the position tracking device may exploit the waves reflected from the wave directing device 18 back towards the position tracking device such as in a pulse-echo mode. In this case, the position tracking device 20 comprises a mechanical wave detector for detecting the mechanical waves reflected by the wave directing device 18 and the position and/or orientation of the wave directing device 18 is determined according the signal detected by the mechanical wave detector, e.g., according the amplitude, the phase and/or the delay of the waves detected by the mechanical wave detector.

In one embodiment, the wave directing device 18 is adapted to reflect or deflect incoming mechanical waves. In this case, the wave directing device 18 may be made of or coated with a material adapted to reflect mechanical waves. Such a reflecting material should have an acoustic impedance being greater than that of surroundings. Since the surroundings include tissues and body fluids which have an acoustic impedance close to that of water, a suitable reflecting material can be any solid such as polymers or metals or composite material. The wave directing device 18 is then adapted to receive mechanical waves being incident thereon according to an incident angle and reflect the incident mechanical waves according to a reflection angle which may be dependent on the incident angle. In one embodiment, the wave directing device is a specular reflector so that the reflection angle of the mechanical waves is equal to the incident angle of the mechanical waves. In this case, the reflection angle may be changed by varying the incident angle. In one embodiment, the wave directing device 18 is further adapted to concentrate or focus the incident mechanical waves towards a focus point. In this case, the wave directing device 18 may be an acoustic mirror.

In another embodiment, the wave directing device 18 is adapted, by a proper combination of materials and geometry, to refract mechanical waves being incident thereon towards a focus point. In this case, the wave directing device 18 may be an acoustic lens.

Figure 2:
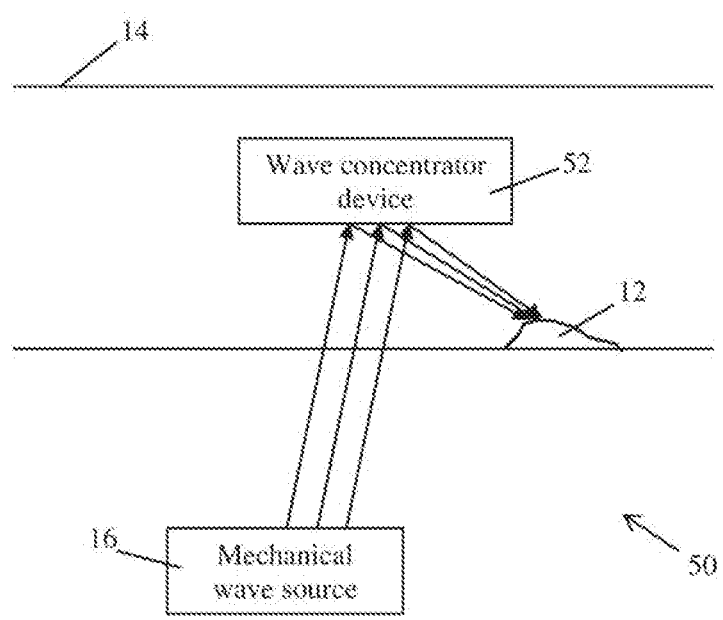
FIG. 2 is a block diagram illustrating a system comprising a source of mechanical waves for externally generating mechanical waves and a wave concentrator device for reflecting and focusing the generated mechanical waves towards a lesion to be treated present in a vessel of a body, in accordance with an embodiment.

FIG. 2 illustrates one embodiment of a system 50 for delivering mechanical waves or shock waves to treat a lesion 12 present in a blood vessel 14. The system 50 comprises a source 16 of mechanical waves or pulses and a wave concentrator device 52. The wave source 16 is positioned outside of the patient's body and emits mechanical waves or pulses towards the wave concentrator device 52. For example, the wave concentrator device 52 may be made of a material adapted to reflect mechanical waves. In another example, the external or internal surface of the wave concentrator device 52 may be coated with a material adapted to reflect mechanical waves.

The mechanical waves generated by the wave generator 16 reach the wave concentrator device 52 which is adapted to reflect the incident waves according to a reflection direction and further concentrate or focus the reflected mechanical waves on a focus point. By adequately positioning the wave concentrator device 52 relative to the lesion 12 and the wave source 16 relative to the wave concentrator device 52, the focus point may be positioned on the lesion 12 to be treated. In one embodiment, the orientation of the wave concentrator device 52 is also adjusted so as to position the focus point on the lesion 12 to be treated.

In one embodiment, at least a section of the external or internal surface of the wave concentrator device 52 has a geometry adapted to concentrate or focus incident mechanical waves. For example, at least a section of the external or internal surface of the wave concentrator devices 52 may have a concave, hemi-spherical or parabolic shape. In this case, the mechanical waves are propagated towards the concave, hemi-spherical or parabolic portion of the wave concentrator devices 52 and the concave, hemi-spherical or parabolic portion reflects the mechanical waves incident thereon while concentrating the reflected mechanical waves on a focus point.

In one embodiment, at least one characteristic of the wave concentrator device 52 may be adjusted to vary the reflection direction of the reflected mechanical waves, the position of the focus point at which the mechanical waves focus and/or the focal size on the lesion, i.e., the surface area of the lesion on which the reflected mechanical waves are incident. For example, the orientation and shape of the wave concentrator device 52 may be changed by adjusting the curvature of the wave concentrator device 52.

Figure 3A:
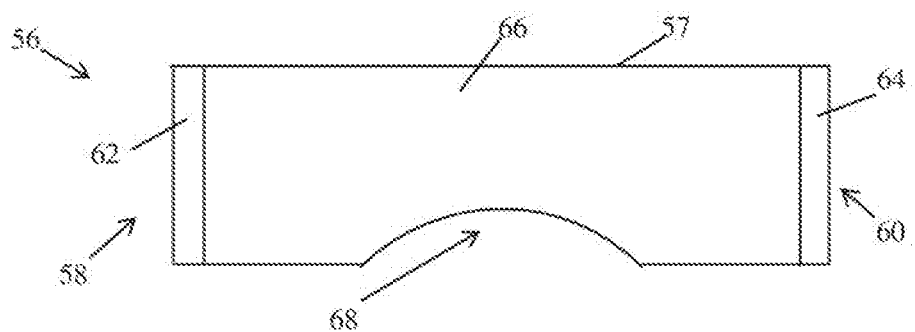
FIG. 3a schematically illustrates a wave concentrator provided having an external surface provided with a concave section, in accordance with an embodiment.

FIG. 3a illustrates one embodiment of a wave concentrator device 56. The wave concentrator device 56 comprises an elongated body 57 which extends between a proximal end 58 and a distal end 60. The elongated body 57 comprises a first marker portion 62 located at the proximal end 58, a second marker portion 64 located at the distal end 60, and a central reflective portion 66 located between the marker portions 62 and 64.

The first and second marker portions 62 and 64 are made of or coated with a marker material such as an X-ray opaque material. Examples of adequate X-ray opaque materials may include platinum, gold, tungsten, alloys of platinum, gold, and tungsten, and polymers doped with platinum, gold or tungsten. The first and second marker portions 62 and 64 then allow an adequate positioning of the wave concentrator device 56 relative to the lesion 12, knowing that the reflective portion of the wave concentrator device 56 is located between the first and second marker portion 62 and 64.

At least one section 68 of the external surface of the central portion 66 is made of or coated with a material adapted to reflect mechanical waves and provided with a concave shape to further focus mechanical waves incident thereon towards a focus point.

In one embodiment, the shape of the reflective section 68 may be adjusted to vary the reflection direction of the reflected mechanical waves, the position of the focus point at which the mechanical waves focus and/or the focal size of the mechanical waves on the lesion 12. For example, the wave concentrator device 56 may comprise any inflatable structure provided with a reflective external surface, such as an inflatable balloon, and the shape of the reflective section 68 may be adjusted by inflating/deflating the balloon within the wave concentrator device 56. For example, the wave concentrator device 56 may be a generally cylindrical or spherical balloon of which principal radius of curvature, and therefore its focal length, may change by varying the inflation pressure of the fluid present within the balloon. In another example, the wave concentrator device 56 may be a balloon of which the shape may be deformed by varying the inflation pressure of the fluid present within the balloon. It should be understood that in this case, the system further comprises a source of fluid fluidly connected to the balloon in order to inflate/deflate the balloon.

Figure 3B:
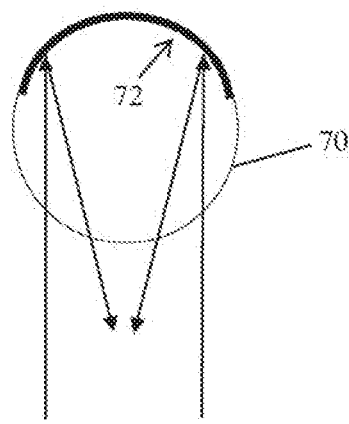
FIG. 3b is a cross-section view of a wave concentrator provided with an internal reflective surface, in accordance with an embodiment.

While FIG. 3a illustrates a wave concentrator device 56 of which the section 68 of the external surface is reflective, thereby playing the role of an acoustic mirror. FIG. 3b illustrates a cross-sectional view of a wave concentrator device 70 of which a section 72 of the internal surface is reflective and adapted to focus incident mechanical waves. As illustrated in FIG. 3b, the internal face of the wave concentrator device 70 has a curved or circular cross-sectional shape and is reflective to act as an acoustic mirror adapted to reflect and focus incident mechanical waves on a focus point.

Figure 4:
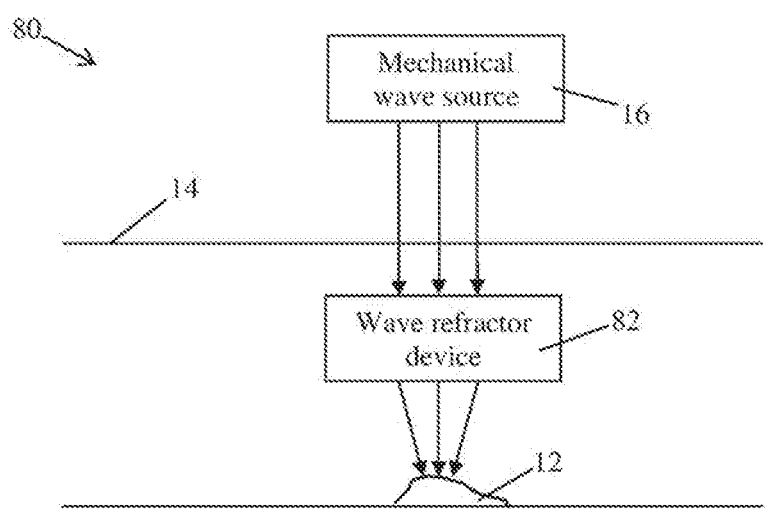
FIG. 4 is a block diagram illustrating a system comprising a source of mechanical waves for externally generating mechanical waves and a wave refractor device for refracting the generated mechanical waves towards a lesion to be treated present in a vessel of a body, in accordance with an embodiment.

FIG. 4 illustrates one embodiment of a system 80 for delivering mechanical waves or shock waves to treat a lesion 12 present in a blood vessel 14. The system 80 comprises a source 16 of mechanical waves or pulses, and a wave refractor device 82. The wave source 16 is positioned outside of the patient's body and emits mechanical waves or pulses towards the wave refractor device 82. For example, the wave refractor device 82 may be made of a material or a combination of materials adapted to refract mechanical or shock waves. The material may have an acoustic impedance different from that of the surroundings (e.g., the acoustic impedance of water) so that the wave refractor device 82 may act as an acoustic lens. Preferably the acoustic impedance of the wave refractor device should be different but not too far from the acoustic impedance of the surrounding tissue and/or body fluids. Exemplary wave refractor materials are polymers and fluids having a different density than water.

The mechanical waves generated by the wave generator 16 reach the wave refractor device 82. The wave refractor device 82 may act as an acoustic lens, i.e., it is adapted to refract the incident waves according to a refractor direction and further concentrate or focus the refractor mechanical waves at a focus point. The geometry and material for the wave refractor device 82 are chosen so that the wave refractor device 82 acts as an acoustic lens. By adequately positioning and orienting the wave refractor device 82 relative to the lesion 12 and the wave source 16 relative to the wave refractor device 82, the focus point may be positioned on the lesion 12 to be treated.

In one embodiment, at least one characteristic of the wave refractor device 82 may be adjusted to vary the refractor direction of the refractor mechanical waves, the position of the focus point at which the mechanical waves focus and/or the focal size on the lesion, i.e., the surface area of the lesion on which the refractor mechanical waves are incident.

Examples of characteristics of the wave refractor device 82 that may be adjusted comprise the shape, thickness and/or curvature of the wave refractor device 82 and the material contained within the wave refractor device 82 such as fluids or liquids that may be contained within the wave refractor device 82.

In one embodiment, the external surface of a stent may act as a refractor (i.e., lens) to focus the energy onto the target to be treated which may be inside or outside the stent.

In one embodiment, the wave directing device comprises a balloon or a catheter adapted to reflect, refract and/or concentrate mechanical waves features as described above. In one embodiment the balloon is filled with a fluid that favors wave reflection, refraction and/or concentration of mechanical waves. The fluid may be any adequate fluid, such as a liquid, having an acoustic impedance different from that the surrounding tissues and/or body fluids, e.g., a fluid or liquid having an acoustic impedance different from that of water. For example, the fluid may be a liquid having a density different from that of water. By inflating and/or deflating the balloon, the shape of the balloon changes, thereby changing the wave reflection, refraction and/or concentration of mechanical waves of the device. In one embodiment, the balloon may act as an acoustic mirror or an acoustic lens, and the location and size of the focal region at the focal point may be changed by changing the shape of the balloon.

In one embodiment, the wave directing device comprises at least two balloons adapted to reflect, refract and/or concentrate mechanical waves features as described above. In one embodiment, each of the balloons is filled with a fluid that favors wave reflection, refraction and/or concentration of mechanical waves. By inflating and/or deflating the balloons, the shape of the balloons change, thereby changing the wave reflection, refraction and/or concentration of mechanical waves of the device. The fluids in the balloons may be similar or may be different such as to produce the desired wave reflection, refraction and/or concentration characteristics.

In one embodiment, the wave directing device may have part of its geometry shaped with serrations such as to produce an acoustic Fresnel lens.

In one embodiment, the geometry of the wave directing device can be adjusted in-situ to change its reflection, refraction and/or focusing properties.

In one embodiment, the wave directing device comprises a combination of refractor and concentrator portions along its length and circumference such that different treatments may be simultaneously applied to a single or multiple lesions using mechanical waves generated by a single source.

In one embodiment, the wave directing device comprises a mechanically resonant structure that can be used to store at least some of the mechanical energy produced by the external mechanical wave source. As known in the art, the mechanically resonant structure may be a mechanical resonator comprising both an inertia device (a mass) and a compliant device (a spring) or a combination of a plurality of these elements. The resonant frequency or frequencies of this resonator is/are tuned to those of the wave such that mechanical wave interaction of the wave with the resonator sets the resonator in motion. This motion stores kinetic and spring energy which can be used thereafter for the other purposes. So in practice the resonator may be a spring-mass or many spring-mass combinations. The stored mechanical energy can be used to perform treatment on the surrounding tissue, by direct mechanical action, such as vibration or impact, or indirect mechanical action such as the release of a drug. In the case of drug release, this can be combined with simultaneous external mechanical energy exposure to promote drug uptake by the target tissue to be treated.

In one embodiment, the minimally-invasive wave directing device further comprises a fluid delivery system comprising one or more liquid delivery tubes to deliver a fluid such as drugs, vaccines or other therapeutic substances to the target to be treated, or to cool/eat the target to be treated, for example. The liquid delivery can be performed before, at the same time or after external mechanical energy exposure. In the case of drug delivery, this can be combined with simultaneous external mechanical energy exposure to promote drug uptake by the lesion to be treated.

In one embodiment, the minimally-invasive wave directing device is coated with drugs, vaccines or other therapeutic substances. The drugs, vaccines or other therapeutic substances can diffuse into the lesion to be treated when the minimally-invasive wave directing device is put in contact with the lesion. Subsequent mechanical energy exposure, may further promote drug uptake by the lesion to be treated. In another embodiment, these drugs, vaccines or other therapeutic substances may be liberated by the action of mechanical energy exposure, which may further promote drug uptake by the lesion to be treated.

In one embodiment, the minimally-invasive wave directing device comprises an encapsulation containing drugs, vaccines or other therapeutic substances. Mechanical energy exposure may release the encapsulation of these drugs, vaccines or other therapeutic substances into the lesion to be treated with which the minimally-invasive wave directing device is in contact. For example, the drugs may be enclosed into a capsule secured to the minimally-invasive wave directing device and the capsule is breakable under the effect of the mechanical waves so as to release the drugs. Subsequent mechanical energy exposure may further promote drug uptake by the lesion to be treated.

In one embodiment, the wave directing device further comprises one or more aspiration tubes for aspirating debris produced by the procedure, for example.

In one embodiment, the wave generator may be focalized, for example by exploiting a properly shaped geometry or by exploiting multiple individual wave generators in a phased array, or an additional stage of focalization may be added between the blood vessel 14 and the source 16 of mechanical waves. For example, the wave generator may be focalized by using an acoustic lens.

In one embodiment, the wave generator may generate different types of mechanical waves, some of which may be more appropriate to treat the lesion and some of which may be more appropriate to locate the wave directing device in a pulse-echo mode in conjunction with a position tracking device.

In one embodiment, the wave directing device further comprises an optical coherence tomography (OCT) or intravascular ultrasound (IVUS) imaging device.

In one embodiment, the wave directing device comprises a drug (or similar) capsule at the distal end thereof that can be triggered (liberated) from the proximal end with a mechanism running along the length of the wave directing device.

In one embodiment, the wave directing device comprises a piezoelectric element that generates electricity when exposed to the mechanical energy produced by the external source.

In one embodiment, the wave directing device comprises one or many frangible elements that can break when exposed to the mechanical energy produced by the external source.

In one embodiment, the external surface of the wave directing device comprises features, such as roughness and/or porosity, that promote local cavitation when exposed to the mechanical energy produced by the external source.

In one embodiment, the external mechanical wave source is in contact with the skin of the patient with an acoustic coupling to maximize energy transmission.

In one embodiment, the external mechanical wave source is arranged circumferentially around an axis. For example the external mechanical wave source could fully or partially wrap around a leg, arm, head or torso.

In one embodiment, the external source of mechanical waves, coupled to a wave concentrator or not, is not adapted to focus enough the mechanical energy to obtain sufficient energy for directly treating the lesion. In this case, the above described wave concentrator device and wave refractor device can further concentrate the mechanical energy delivered by the source of mechanical in order to achieve an amount of energy concentration that is adequate for treating the lesion.

Figure 5:
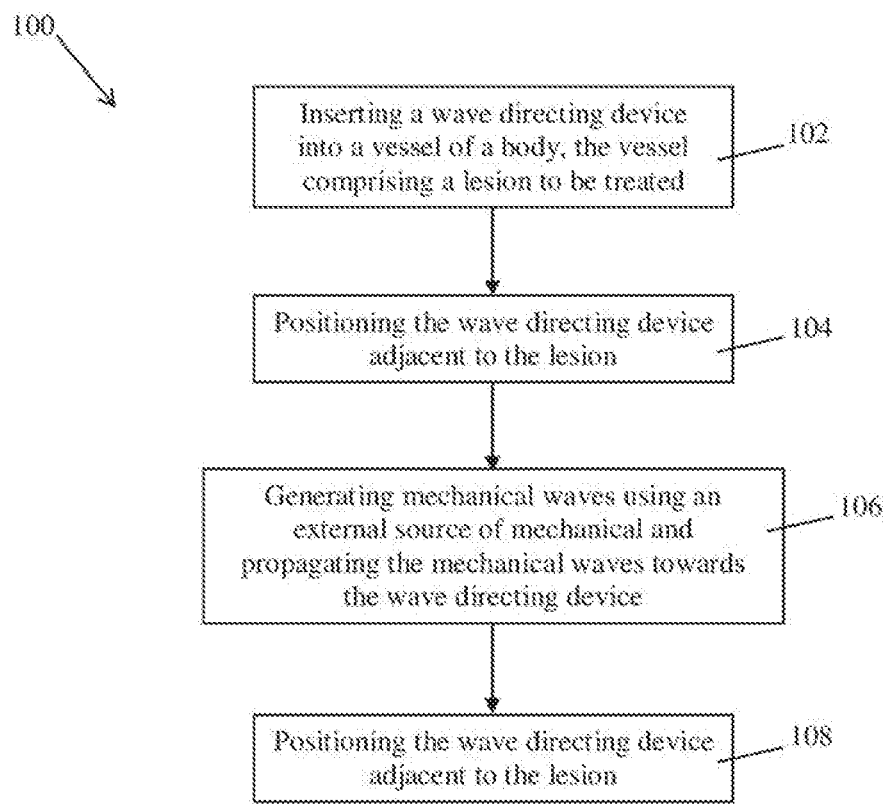
FIG. 5 is flow chart illustrating a method for treating a lesion present in a vessel of a body, in accordance with an embodiment.

FIG. 5 illustrates one embodiment of a method 100 for treating a lesion present in a vessel of a body.

At step 102, a wave directing device is inserted into the vessel of the body and positioned adjacent to the lesion to be treated at step 104. The wave directing device is positioned and oriented according to a desired position and a desired orientation relative to the lesion to be treated. The desired position and orientation are chosen so that mechanical waves incident on the wave directing device propagate towards the lesion to be treated.

At step 106, mechanical waves are generated using an external source of mechanical waves located outside of the body and the generated mechanical waves are propagated towards the wave directing device.

At step 108, the mechanical waves incident on the wave directing device are redirected and concentrated on the lesion, thereby treating the lesion.

In one embodiment, the step of redirecting the mechanical waves comprises reflecting the mechanical waves. In this case, the wave directing device is adapted to reflect and concentrate the mechanical waves received from the external mechanical wave source, as described above. For example, the wave directing device may be an acoustic mirror.

In another embodiment, the step of redirecting the mechanical waves comprises refracting the mechanical waves. In this case, the wave directing device is adapted to refract and concentrate the mechanical waves received from the external mechanical wave source, as described above. For example, the wave directing device may be an acoustic lens.

In an embodiment in which the wave directing device is an inflatable balloon, the method 100 further comprises the step of inflating or deflating the balloon to obtain a desired shape for the balloon prior to generating the mechanical waves. As described above, the balloon may be adapted to reflect mechanical waves or refract mechanical waves.

In an embodiment in which the wave directing device is secured to an elongated member, the step 104 of positioning the wave directing device comprises manipulating the proximal end of the elongated member, i.e. pushing, pulling and/or rotating the distal end of the elongated member.

In one embodiment, the method 100 further comprise, a step of detecting at least one of a position and an orientation of the wave directing device once inserted into the vessel using a position tracking device.

In one embodiment, the detection of the position and/or orientation of the wave directing device is performed using an X-Ray imaging device or an ultrasound imaging device.

In another embodiment, the detection of the position and/or orientation of the wave directing device is performed by detecting mechanical waves reflected by the wave directing device using a mechanical wave detector and determining the at least one of the position and the orientation from the amplitude, phase and/or delay of the mechanical waves detected by the mechanical wave detector.

The embodiments of the invention described above are intended to be exemplary only. The scope of the invention is therefore intended to be limited solely by the scope of the appended claims.

We claim:

1. A system for delivering high amplitude and broadband pulsed mechanical waves to treat a lesion present in a vessel of a body, comprising:
   an external mechanical wave source configured for generating high amplitude and broadband pulsed mechanical waves from outside of the body, the high amplitude and broadband pulsed mechanical waves having an amplitude between 10 MPa and 1000 MPa and a duration of 1/fc, fc being a center frequency between 20 kHz and 10 MHz; and
   a wave refractor device insertable in the vessel, the wave refractor device comprising at least one inflatable balloon comprising a respective fluid having a respective acoustic impedance, the wave refractor device being positionable and orientable within the vessel independently from and relative to the external mechanical wave source, the wave refractor device being configured for receiving the high amplitude and broadband pulsed mechanical waves generated by the external mechanical wave source and act as an acoustic lens by refracting and concentrating the high amplitude and broadband pulsed mechanical waves towards a focus point according to a target location by changing a shape of the at least one inflatable balloon via the respective fluid, the wave directing device being positionable and orientable inside the vessel relative to the lesion for selecting the target location during treatment for redirecting the high amplitude and broadband pulsed mechanical waves to the focus point to treat the lesion.

2. The system of claim 1, wherein the wave refractor device comprises a least one section having one of a concave, convex, spherical, hemi-spherical or parabolic shape.

3. The system of claim 1, wherein the wave refractor device is made of a material having an acoustic impedance being different from an acoustic impedance of water.

4. The system of claim 1, wherein the wave refractor device comprises at least one marker visible on a medical image.

5. The system of claim 4, wherein the marker is made of a radiopaque material.

6. The system of claim 1, further comprising a source of fluid fluidly connected to the inflatable balloon for injecting the respective fluid within the inflatable balloon so as to change the shape of the balloon.

7. The system of claim 1, further comprising an elongated member, the wave refractor device being removably or integrally secured to the elongated member.

8. The system of claim 7, wherein the elongated member comprises a catheter.

9. The system of claim 1, further comprising a position tracking device for tracking at least one of a position and an orientation of the wave refractor device once inserted into the vessel of the body.

10. The system of claim 9, wherein the position tracking device comprises one of an X-Ray imaging device and an ultrasound imaging device.

11. The system of claim 9, wherein the position tracking device comprises a mechanical wave detector for detecting mechanical waves reflected by the wave refractor device, the at least one of the position and the orientation of the wave refractor device being determined according to at least one of an amplitude, a phase and a delay of mechanical waves detected by the mechanical wave detector.

12. The system of claim 1, wherein the wave refractor device comprises a mechanically resonant structure for storing or restituting mechanical energy.

13. The system of claim 6, wherein changing the shape of the balloon causes changing at least one of a size and a location of a focal region of the focus point.

14. The system of claim 1, wherein the wave refractor device has at least one of an adjustable shape and an adjustable curvature for refracting and concentrating the high amplitude and broadband pulsed mechanical waves towards the focus point according to the target location.

15. The system of claim 6, wherein the at least one inflatable balloon comprises at least two inflatable balloons each comprising a respective fluid having a respective acoustic impedance different from the acoustic impedance of surrounding tissues.

16. The system of claim 3, wherein the material comprises a polymer.

17. A method for treating a lesion, comprising:
inserting a wave refractor device into a vessel of a body, the wave refractor device comprising at least one inflatable balloon comprising a respective fluid having a respective acoustic impedance, the vessel comprising a lesion to be treated;
positioning the wave refractor device adjacent to the lesion to be treated, the positioning comprising orienting the wave refractor device relative to an external mechanical wave source located outside of the body;
generating high amplitude and broadband pulsed mechanical waves using the external mechanical wave source and propagating the high amplitude and broadband pulsed mechanical waves towards the wave refractor device, the high amplitude and broadband pulsed mechanical waves having an amplitude between 10 MPa and 1000 MPa and a duration of 1/fc, fc being a center frequency between 20 kHz and 10 MHz; and
at the wave refractor device, positioning, orienting and changing a shape of the inflatable balloon of the wave refractor device to refract and concentrate the high amplitude and broadband pulsed mechanical waves according to a selected location towards a focus point on the lesion to be treated.

* * * * *